(12) United States Patent
Khalaj

(10) Patent No.: US 10,195,399 B2
(45) Date of Patent: Feb. 5, 2019

(54) CATHETER SECUREMENT DEVICE

(71) Applicant: Avent, Inc., Alpharetta, GA (US)

(72) Inventor: Steve Saeed Khalaj, Laguna Hills, CA (US)

(73) Assignee: Avent, Inc., Alpharetta, GA (US)

( * ) Notice: Subject to any disclaimer, the term of this patent is extended or adjusted under 35 U.S.C. 154(b) by 899 days.

(21) Appl. No.: 14/066,061

(22) Filed: Oct. 29, 2013

(65) Prior Publication Data

US 2015/0119808 A1    Apr. 30, 2015

(51) Int. Cl.
*A61M 25/02* (2006.01)

(52) U.S. Cl.
CPC ....... *A61M 25/02* (2013.01); *A61M 2025/024* (2013.01); *A61M 2025/0246* (2013.01); *A61M 2025/0273* (2013.01)

(58) Field of Classification Search
CPC .. A61M 2025/0273; A61M 2025/0246; A61M 2025/024
See application file for complete search history.

(56) References Cited

U.S. PATENT DOCUMENTS

| | | | |
|---|---|---|---|
| 3,581,732 A | 6/1971 | Ruiz | |
| 3,683,928 A * | 8/1972 | Kuntz | A61M 25/0111 206/364 |
| 4,659,329 A | 4/1987 | Annis | |
| 4,959,055 A | 9/1990 | Hillyer | |
| 4,973,314 A | 11/1990 | Garrett | |
| 5,690,616 A | 11/1997 | Mogg | |
| 6,387,076 B1 * | 5/2002 | Landuyt | A61M 25/02 128/DIG. 6 |
| 6,929,624 B1 | 8/2005 | Del Castillo | |
| 7,580,756 B2 * | 8/2009 | Schulte | A61N 1/0539 606/129 |
| 7,604,644 B2 * | 10/2009 | Schulte | A61N 1/0539 604/175 |
| 7,635,355 B2 | 12/2009 | Bierman | |

(Continued)

FOREIGN PATENT DOCUMENTS

| | | |
|---|---|---|
| EP | 0 931 560 | 7/1999 |
| WO | WO 03/068304 A1 | 8/2003 |

(Continued)

*Primary Examiner* — Theodore Stigell
*Assistant Examiner* — Matthew A Engel
(74) *Attorney, Agent, or Firm* — Dority & Manning, P.A.

(57) ABSTRACT

The present invention relates to a catheter securement device and securement device assembly for a securing a catheter relative to a patient. The securement device includes a base having an opening configured for receipt of the catheter, a cover member configured with the base over the opening, and a lip configured around at least a portion of the base. The base is configured for attachment to a patient's skin over a catheter insertion site and includes a top surface and a bottom surface. The opening of the base is configured to accommodate a catheter inserted therethrough from the catheter insertion site. The cover member is movable from an open position to a closed position over the catheter insertion site and is configured to secure the catheter. The lip is configured on the bottom surface of the base around the opening such that the lip reduces leakage from the catheter insertion site when the securement device is secured to the patient's skin.

17 Claims, 5 Drawing Sheets

(56) References Cited

U.S. PATENT DOCUMENTS

| | | | |
|---|---|---|---|
| 7,749,199 B2* | 7/2010 | Mogg | A61M 25/02 604/174 |
| 8,052,649 B2 | 11/2011 | Wright | |
| 8,177,756 B2 | 5/2012 | Wright | |
| 8,366,683 B2 | 2/2013 | Patton | |
| 8,465,458 B2 | 6/2013 | Bierman | |
| 8,500,698 B2 | 8/2013 | Kyvik et al. | |
| 8,684,974 B2 | 4/2014 | Richard | |
| 2003/0093075 A1 | 5/2003 | Levinson | |
| 2005/0113761 A1 | 5/2005 | Faust et al. | |
| 2005/0182420 A1* | 8/2005 | Schulte | A61N 1/0539 606/130 |
| 2005/0182421 A1* | 8/2005 | Schulte | A61N 1/0539 606/130 |
| 2005/0182422 A1* | 8/2005 | Schulte | A61N 1/0539 606/130 |
| 2005/0182423 A1* | 8/2005 | Schulte | A61N 1/0539 606/130 |
| 2005/0182424 A1* | 8/2005 | Schulte | A61N 1/0539 606/130 |
| 2005/0182425 A1* | 8/2005 | Schulte | A61N 1/0539 606/130 |
| 2005/0182464 A1* | 8/2005 | Schulte | A61N 1/0539 607/115 |
| 2008/0243085 A1 | 10/2008 | DeStefano | |
| 2008/0312598 A1 | 12/2008 | Douglas et al. | |
| 2009/0187149 A1* | 7/2009 | Nelson | A61M 39/0247 604/175 |
| 2009/0192467 A1 | 7/2009 | Hansen et al. | |
| 2011/0034981 A1* | 2/2011 | Schulte | A61N 1/0539 607/116 |
| 2012/0245529 A1* | 9/2012 | Hummen | A61M 25/02 604/175 |

FOREIGN PATENT DOCUMENTS

| | | |
|---|---|---|
| WO | WO 2008/119041 A1 | 10/2008 |
| WO | WO 2012/020246 A1 | 2/2012 |

* cited by examiner

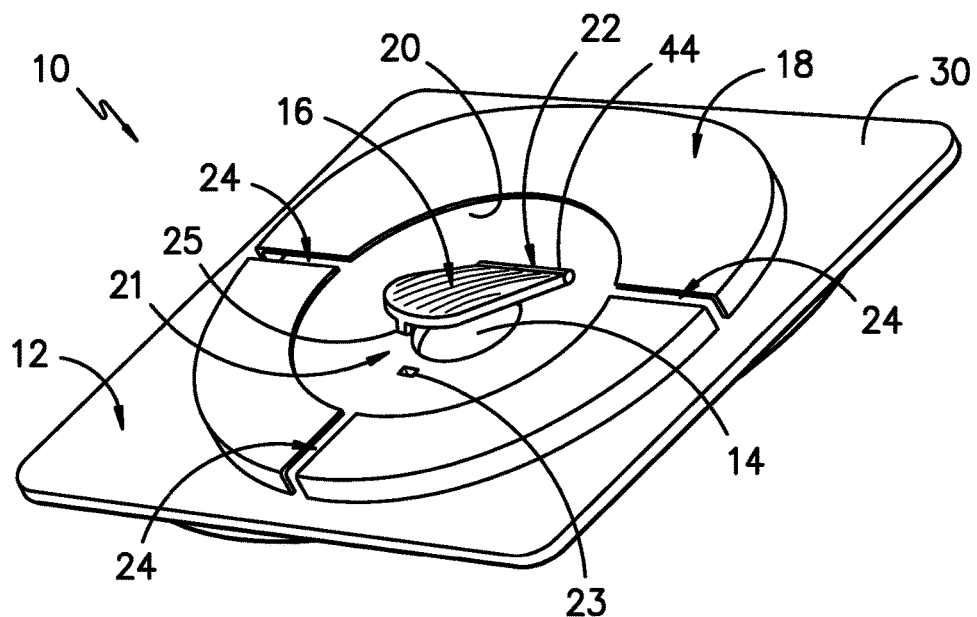
FIG. -1-
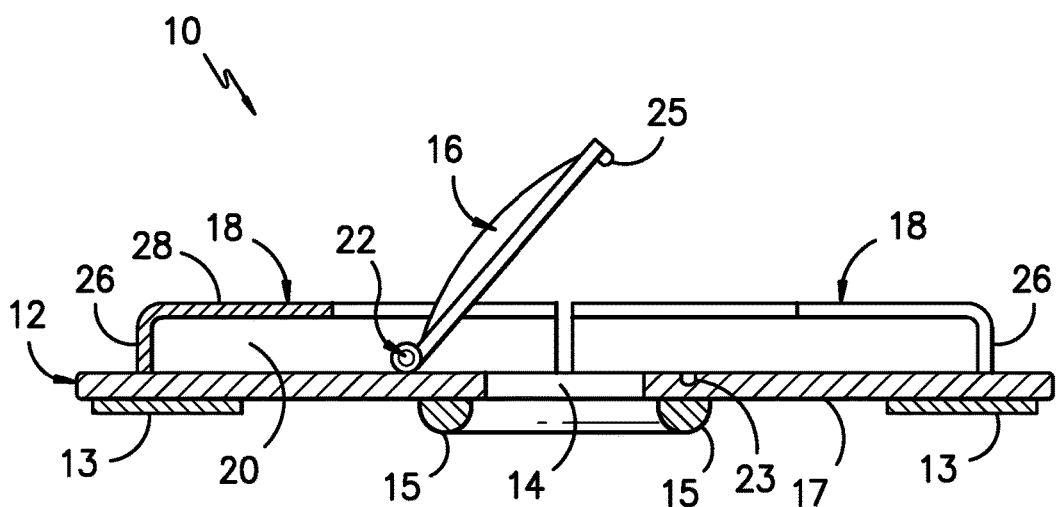
FIG. -2-

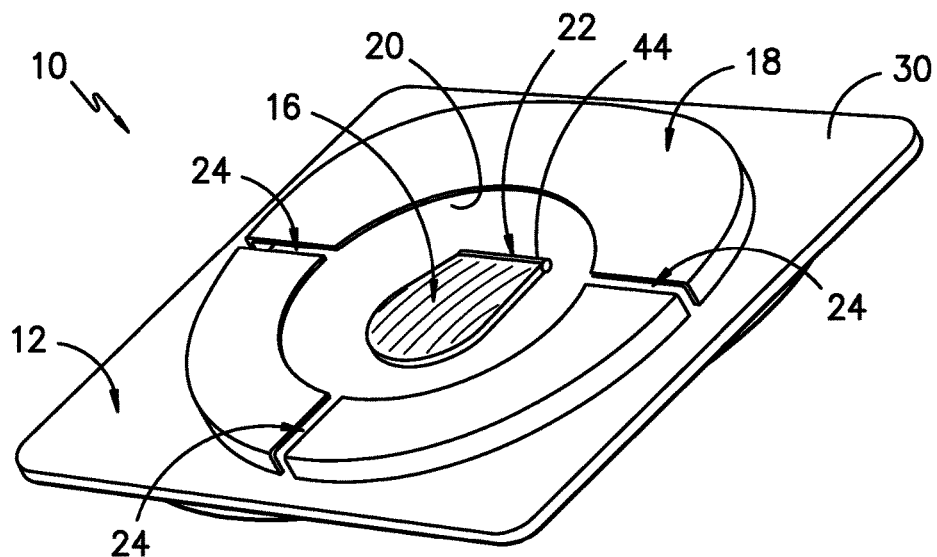
FIG. -3-
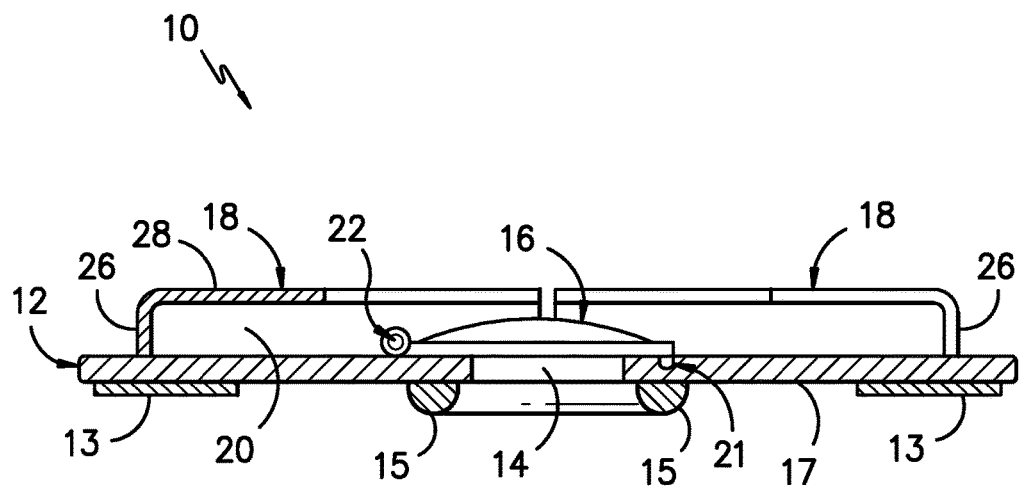
FIG. -4-

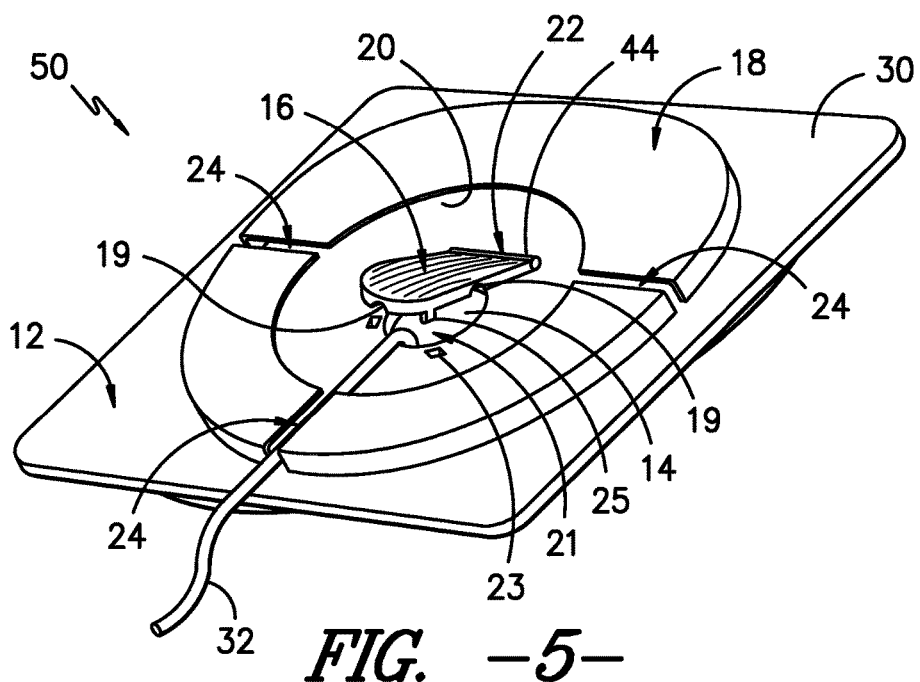
FIG. -5-
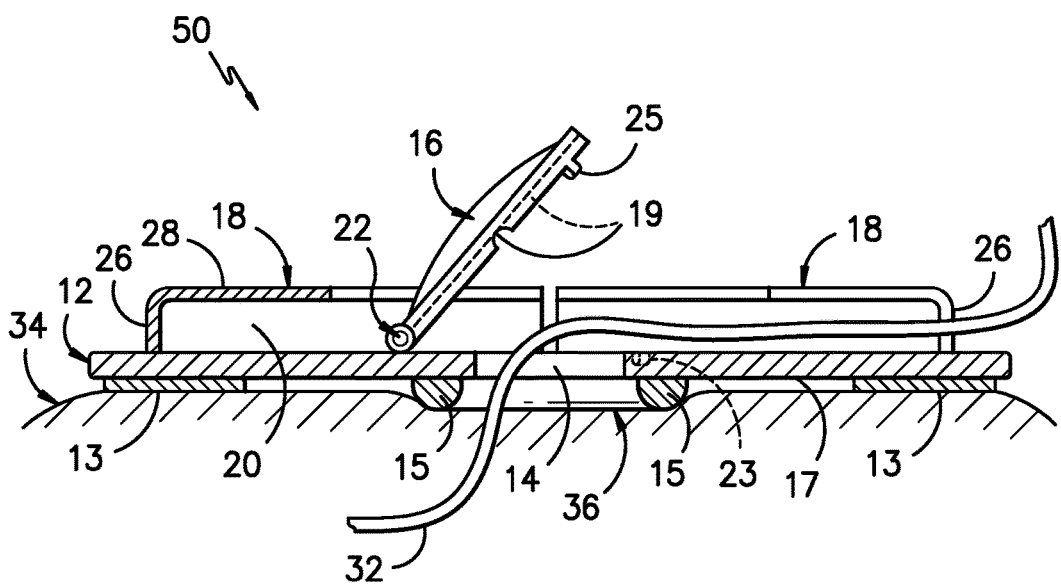
FIG. -6-

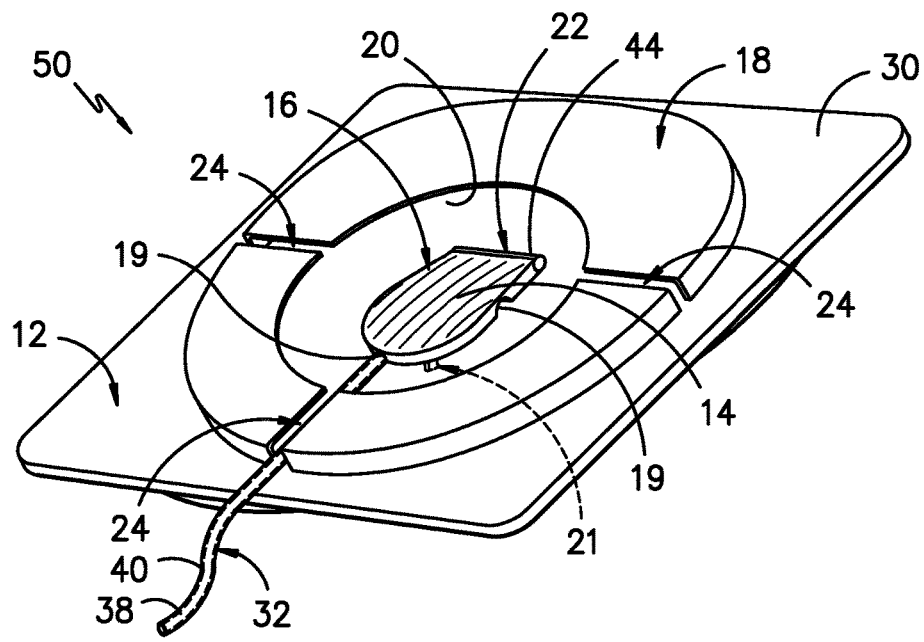
FIG. -7-
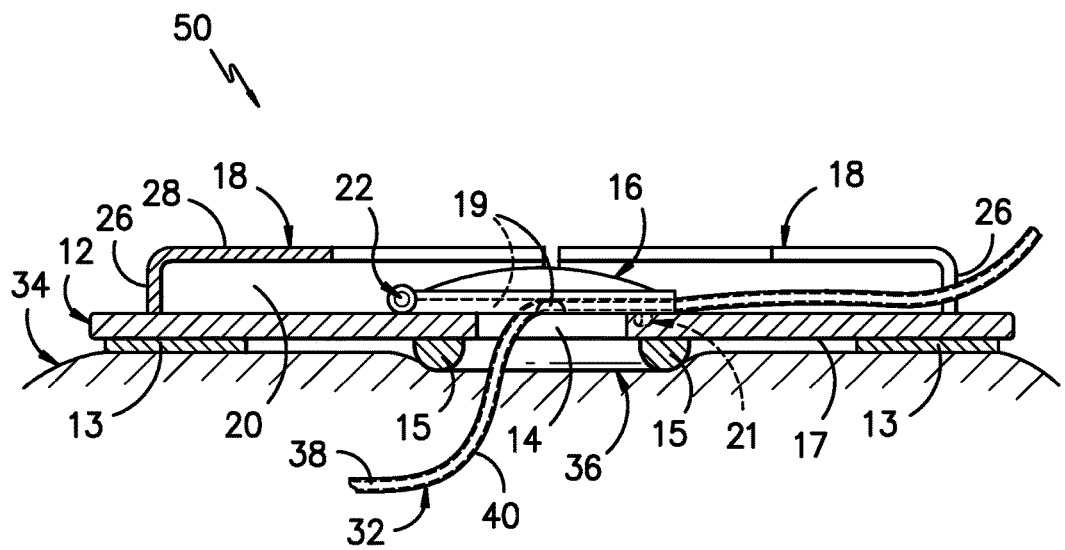
FIG. -8-

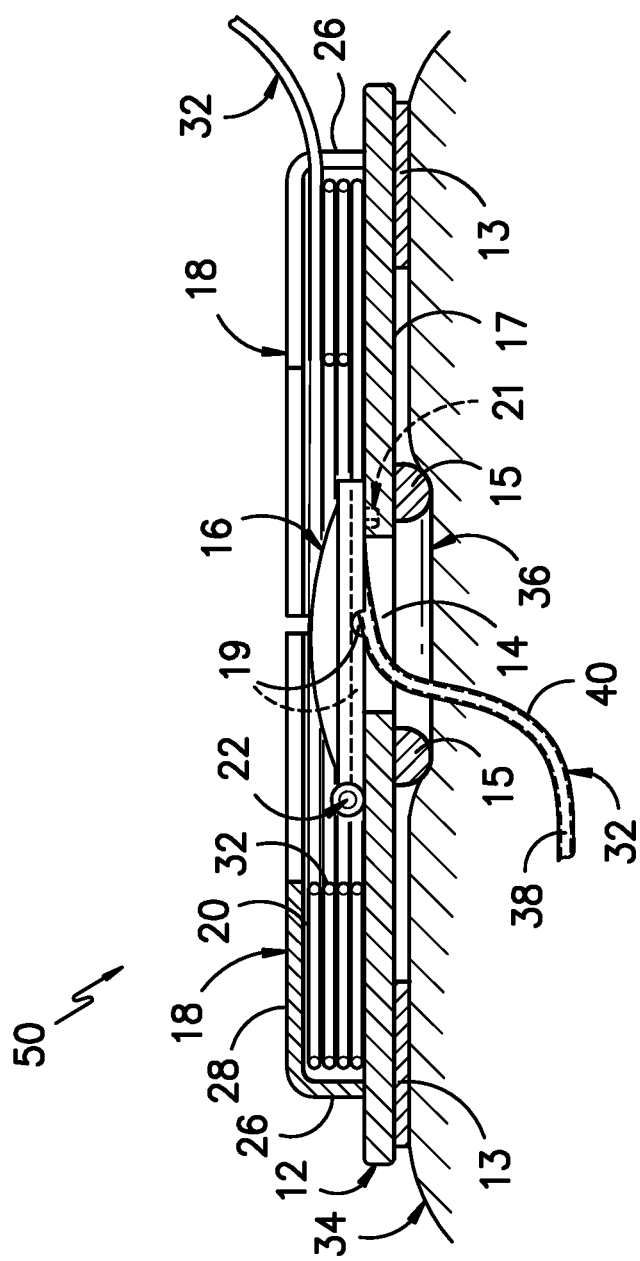
FIG. -9-

CATHETER SECUREMENT DEVICE

FIELD OF THE INVENTION

The present invention relates generally to the field of medical catheters and more particularly to securement devices for catheters.

BACKGROUND

The use of catheters to deliver or withdraw fluids from a patient for various medical procedures is well known. For example, U.S. Pat. No. 7,959,623 describes a pain management system that uses various embodiments of infusion catheters to deliver fluid medication from a pump, through tubing, to a wound site. With such systems, catheter connectors are typically used to connect the catheter to various devices, such as tubing, a fluid reservoir or other fluid delivery device, and so forth.

Often, the use of such catheters must be maintained over extended treatment time periods. It has been a well-known practice to secure these catheters with tape. However, the use of a tape dressing can be problematic in that, among other drawbacks, such dressings must be frequently changed, which can irritate the skin around the catheter insertion site and lead to build up of adhesive on the catheter. This adhesive can result in contaminates adhering to the catheter, and can render the catheter difficult to handle.

In this regard, devices have been developed to secure a catheter to the patient without excessive use of tape. One such device is the "Grip-Lok™" securement device from Zefon International Inc. of Ocala, Fla., USA. This device includes an adhesive base layer that attaches to the patient's skin. The catheter or catheter/connector combination is pressed onto an adhesive pad attached to an upper surface of the base layer. A Velcro™ closure layer is then folded over the catheter and attaches to the upper surface of the base layer.

U.S. Pat. No. 7,635,355 describes a medical line securement device for securing a catheter connector on the patient's body. The device includes an anchor pad that attaches to the patient's skin, with a retainer attached to an upper surface of the pad. The retainer has a base member and a cover hinged to the base member and movable between an open and latch-closed position. The base and cover each have respective grooves that cooperate to form a channel in the closed position of the cover. The connector has an elongated body that is received in the channel, whereby axial motion of the connector is inhibited by engagement of the connector within the closed retainer.

The medical art is thus continuously seeking new and improved securement devices for securing catheters relative to a patient for extended periods of time without discomfort to the patient. The present invention provides such a device.

SUMMARY OF THE INVENTION

Objects and advantages of the invention will be set forth in part in the following description, or may be obvious from the description, or may be learned through practice of the invention.

In certain aspects, the present invention relates to a securement device for a catheter. The securement device includes a base having an opening configured for receipt of the catheter, a cover member configured with the base over the opening, and a lip configured around at least a portion of the opening. The base is configured for attachment to the patient's skin over a catheter insertion site and includes a top surface and a bottom surface. The opening of the base is configured to accommodate a catheter inserted therethrough from the catheter insertion site. The cover member is configured with the base over the opening and is movable from an open position to a closed position over the catheter insertion site. Further, the cover member is configured to secure the catheter. The lip is configured on the bottom surface of the base around the opening such that the lip reduces leakage from the catheter insertion site when the securement device is secured to the patient's skin.

In a further embodiment, the cover member is hinged to the base at a hinge line. In an additional embodiment, the securement device may include a latch device. As such, the cover member is configured to latch to the said base via the latch device when the cover member is in the closed position. Further, the cover member may include one or more grooves configured to accommodate the catheter. As such, the grooves are configured to frictionally engage the catheter without compromising a lumen of the catheter.

In still further embodiments, the lip surrounds the opening such that when the base is secured to the patient's skin, the lip forces the patient's skin around the catheter to form a seal and reduce leakage from the catheter insertion site. In addition, the lip may include any suitable cross-sectional shape. For example, in one embodiment, the lip has an arcuate cross-sectional shape.

In yet another embodiment, the securement device further includes a housing configured on the base. As such, in a particular embodiment, the housing and the base may define an interior space configured to house at least a portion of the catheter. Further, the housing is configured such that the catheter coils within the interior space. In still a further embodiment, the housing further includes one or more slots configured to receive the catheter. For example, in one embodiment, the housing includes at least three slots, wherein each of the slots is spaced approximately ninety degrees apart from another slot. In still additional embodiments, the slots may be spaced apart any suitable distance. In still a further embodiment, the housing further includes a perimeter wall and a top wall. More specifically, the perimeter wall may extend from the base and the top wall may be parallel to the top surface of the base. As such, the perimeter wall, the top wall, and the top surface of the base form the interior space configured to house at least a portion of the catheter.

In additional embodiments, the housing may be integral with the base or may be a separate feature attached to the base. In still further embodiments, the base may further include an attachment pad connected to the lower surface of the base. The attachment pad may include an adhesive lower surface for attachment to the patient's skin.

In a further aspect, a securement device assembly is disclosed. The securement device assembly includes a catheter and a securement device. The catheter generally includes a proximal end, a distal end, and walls defining a lumen. The securement device may include a base having an opening configured for receipt of the catheter from a catheter insertion site, a cover member configured with the base over the opening, and a lip configured around at least a portion of the opening. The base is configured for attachment to the patient's skin over the catheter insertion site and includes a top and bottom surface. The cover member is movable from an open position to a closed position over the catheter insertion site. Further, the cover member is configured to secure the catheter. The lip is configured on the bottom surface of the base and reduces leakage from the wound site when the securement device is secured to the patient's skin. It should be understood that the securement device assembly may further include any of the features described herein.

Various embodiments of such a securement device are discussed above and set forth in greater detail below. These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

FIG. 1 is a perspective view of one embodiment of a catheter securement device in an open position in accordance with aspects of the invention;

FIG. 2 is a cross-sectional view of the catheter securement device of FIG. 1;

FIG. 3 is a perspective view of another embodiment of the catheter securement device in a closed position in accordance with aspects of the invention;

FIG. 4 is a cross-sectional view of the catheter securement device of FIG. 3;

FIG. 5 is a perspective view of one embodiment of a securement device assembly in an open position in accordance with aspects of the invention;

FIG. 6 is a cross-sectional view of the securement device assembly of FIG. 5;

FIG. 7 is a perspective view of the embodiment of FIG. 5 in a closed position;

FIG. 8 is a cross-sectional view of the securement device assembly of FIG. 7; and FIG. 9 is a cross-sectional view of another embodiment of a securement device assembly.

DETAILED DESCRIPTION OF THE INVENTION

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

Generally, the present disclosure involves a catheter securement device and assembly for securing a catheter relative to a patient over a catheter insertion site so as to prevent leakage from the catheter insertion site. More specifically, the securement device includes a lip on a patient-side of the securement device, such that when the securement device is secured to the patient, the lip places pressure on the patient's skin so as to force the skin around the catheter to form a seal. As such, the lip is configured to prevent leakage from the catheter insertion site. In addition, the securement device may include a cover member to further prevent leakage from escaping the catheter insertion site or contaminants from entering into the catheter insertion site.

Referring to the drawings, FIGS. 1-9 illustrate various views of a catheter securement device 10 and securement device assembly 50 in accordance with aspects of the invention. More specifically, FIGS. 1-2 illustrate the catheter securement device 10 in an open position, whereas FIGS. 3-4 illustrate the catheter securement device 10 in a closed position. FIGS. 5-6 illustrate the securement device assembly 50 in an open position relative to a patient's skin, whereas FIGS. 7-8 illustrate the securement device assembly 50 in a closed position relative to the patient's skin. FIG. 9 illustrates the securement device assembly 50 having a coiled catheter stored therein.

As shown generally in the figures, the securement device 10 includes a base 12, a cover member 16, and an annular lip 15. The base 12 includes a top surface 30 and a bottom surface 17. The bottom surface 17 is configured for attachment to a patient's skin 34 over a catheter insertion site 36. In addition, the base 12 includes an opening 14 configured to accommodate the catheter 32 inserted therethrough from the catheter insertion site 36. The base 12 and opening 14 may have any suitable shape. For example, in the illustrated embodiment, the base 12 has a generally square configuration; however, this is for illustrative purposes only. In further embodiments, the base 12 may have a rectangular, oval, circular, or any other type of overall shape and configuration. Similarly, the opening 14 may be any suitable shape so as to accommodate the catheter 32 inserted therethrough, including but not limited to a square, rectangle, triangle, circle, oval, or any other shape. For example, as shown, the opening 14 has a generally circular shape.

Referring particularly to FIGS. 2, 4, 6, and 8, the lip 15 is configured to reduce leakage from the catheter insertion site 36. As shown, the lip 15 is configured on a bottom surface 17 of the base 12 at least partially around the opening 14 such that the lip 15 contacts the patient's skin. More specifically, and referring to FIGS. 6 and 8, the lip 15 applies a suitable pressure to the patient's skin 34 so as to force the patient's skin 34 around the catheter 32, thereby forming a seal with the catheter 32. Accordingly, the lip 15 is configured to reduce leakage from the catheter insertion site 36.

In various embodiments, the lip 15 may completely surround the opening 14 or may only surround a portion or portions of the opening 14. In still further embodiments, the perimeter shape of the lip 15 may be annular, rectangular, square, triangular, or any other suitable shape. In addition, the perimeter shape of the lip 15 may be determined according to the shape of the opening 14. It should also be understood that the lip 15 may have any suitable cross-sectional shape so as to force the patient's skin 34 around the catheter. For example, as shown in the illustrated embodiments, the lip 15 has a rounded or arcuate cross-sectional shape and extends annularly around the opening 14 of the base 12. In still further embodiments, the lip 15 may have a rectangular or square cross-sectional shape. In addition, the lip 15 may be constructed of any suitable material so as to provide the suitable pressure to the patient's skin, while also being comfortable to the patient. For example, in one embodiment, the lip is constructed of a rubber or silicon material.

In further embodiments, the cover member 16 may be configured with the base 12, the housing 18, or any other suitable location on the device 10 and is movable between the open position (FIGS. 1-2) and the closed position (FIGS. 3-4) over the opening 14 so as to cover the catheter insertion site 36. For example, in the illustrated embodiments, the cover member is configured with the base 12. In still further embodiments, as shown, the securement device 10 may include a latch device 21 such that the cover member 16 can be secured to the base 12 via the latch device 21 when the cover member 16 is in the closed position. As such, the cover member 16 may also assist in preventing leakage from the catheter insertion site 36 when in the closed position. The cover member 16 latches to the base 12 by means of any suitable mechanism. For example, one such mechanism may include a latch slot 23 defined in the base 12 that is engaged by an overhanging flange 25 on the cover member 16. Another example of a mechanism is frictional engagement of a portion of the cover member 16 with a portion of the base 12, the housing 18 or both. In addition, the cover member 16 may be hinged to the base 12 at a hinge line 22 such that the cover member 16 is pivotal from the open position to the closed position over the catheter insertion site 36. More specifically, in the embodiments illustrated in the figures, the hinge line 22 may be defined by a rod 44 on the cover member 16 that engages between flanges formed on the base 12. It should be understood, however, that the open and closed positions of the securement device 10 are not limited to any particular hinge mechanism, but may include any suitable hinge mechanism, including a living hinge.

In addition, the cover member 16 is also configured to secure the catheter 32 relative to the patient. For example, in one embodiment, the cover member 16 may include one or more grooves 19 configured to accommodate and secure the catheter 32 relative to the patient. For example, as shown in FIGS. 5-8, the grooves 19 are shaped so as to correspond with the tubing of the catheter 32 such that the catheter 32 fits within one of the grooves 19. As such, the grooves 19 are configured to frictionally engage the catheter 32 without compromising a lumen 38 of the catheter 32.

Still referring generally to the figures, the securement device 10 may also include a housing 18 generally configured to house and/or store the catheter 32. More specifically, in one embodiment, the housing is generally configured on a top surface 30 of the base 12 around the opening 14 and defines an interior space 20 configured to store at least a portion of the catheter 32. For example, in one embodiment, the interior space 20 has a generally circular configuration so as to store the catheter 32 in a coiled state as depicted in FIG. 9. More specifically, the housing 18 may include an outermost circular or annular perimeter wall 26 and a corresponding annular top wall 28. For the embodiments shown in the figures, the perimeter wall 26 is substantially perpendicular to the base 12; however the perimeter wall 26 may extend from the base at a slant. In addition, the top wall 28 also extends towards the opening 14 and is joined to the perimeter wall 26 to create an annular interior space 20 that promotes the inserted portions of catheter 32 to coil within the interior space 20. As such, the perimeter wall 26, the top wall 28, and a portion of a top surface 30 of the base 12 may form the interior space 20 for the catheter 32. As such, any excess catheter tubing may be housed and/or stored with the interior space 20 while the securement device 10 is being used, as shown in FIG. 9. For example, in one embodiment, the inherent flexibility and rigidity of the catheter 32 allows it to coil within the interior space 20 and be stored therein. It should also be understood, however, that the housing 18 may have any suitable shape and/or configuration, including but not limited to a square, rectangular, oval, or similar shape. In still further embodiments, the housing 18 may be integral with the base 12 or may be a separate structure that is attached to the base 12. In alternative embodiments, the base 12 may be eliminated altogether such that the housing 18 itself is configured for attachment to a patient's skin 34 over a catheter insertion site 36 and for storage of the catheter 32.

In additional embodiments, the housing 18 may also include at least one slot 24 configured to receive the catheter 32 so as to position the catheter 32 is a particular direction relative to the patient. As such, the slot 24 may be located at any location on the housing 18. In a further embodiment, the housing 18 may include a plurality of slots 24. For example, as shown in FIGS. 5-8, the housing 18 includes at least three slots 34. Further, each of the slots 24 may be spaced any suitable distance apart from any other slot 24. For example, as shown, each of the slots is located approximately ninety degrees apart from another slot 24. As such, the catheter 32 can be stored and secured in a variety of positions relative to the patient. Such a feature provides a securement device that may be easily coupled with other components, such as a catheter connector, a fluid delivery device, or similar.

In addition, the securement device 10 as described herein provides simple attachment and securing means for the catheter 32. For example, when the cover member 16 is in the open position, the catheter 32 can be inserted through the opening 14 of the base 12 from the catheter insertion site 36. Excess catheter tubing may then be housed in the interior space 20 of the housing 18, e.g., coiled therein. The catheter 32 can then be positioned within one of the desired slots 24 depending on the desired direction of the catheter 32 relative to the patient. The cover member 16 can then be moved to the closed position and secured via the latch device 21. As such, the relatively snug fit between the slot 24 and the catheter 32, as well as engagement of the catheter 32 with the groove 19 of the cover member 16 secures the catheter 32 relative to the patient without the use of tape. Moreover, the securement device 10 provides little or no relative movement of the catheter 32 between the components relative to the patient.

Referring particularly to FIGS. 5-8, the base 12 may also include an attachment pad 13 connected to the lower surface 17 of the base 12. The attachment pad 13 may be made of any suitable material so as to adhere the securement device 10 to the patient's skin 34. For example, in one embodiment, the attachment pad 13 may be a foam pad, for adhering the securement device 10 to the patient's skin 34. Further, the attachment pad 13 may have an adhesive lower surface for attachment to the patient's skin 34. For example, the attachment pad 13 may include any suitable medical grade adhesive covered by a release layer, as is understood by those skilled in the art. In addition, the attachment pad 13 may be any suitable shape and/or configuration suitable to attach the securement device 10 to a patient's skin 34. For example, in one embodiment, the attachment pad 13 may follow a perimeter of the base 12, providing space for the lip 15. In still another embodiment, the attachment pad 13 may cover only a portion of the lower surface 17 of the base 12 or may cover the entire lower surface 17 of the base 12. In another embodiment, the adhesive pad may include lip 15 (as an alternative to including lip 15 on the lower surface of base 12).

It should be further appreciated that aspects of the present invention also encompass various embodiments of the securement device 10 as part of a securement device assembly 50 (e.g., including the catheter 32 and/or a catheter connector). In this regard, the discussion set forth above of the securement device 10 is relevant to the securement device assembly 50 in accordance with aspects of the invention.

While the present invention has been described in connection with certain preferred embodiments it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. A securement device for a catheter, said securement device comprising:
   a base configured for attachment to a patient's skin over a catheter insertion site, said base comprising a top surface, a bottom surface, and a central opening configured to accommodate the catheter inserted therethrough from the catheter insertion site;
   a cover member attached to said base over said opening, said cover member movable from an open position to a closed position over the catheter insertion site, said cover member configured to secure the catheter in place;
   an annular lip configured around at least a portion of said opening on said bottom surface of said base, wherein said lip is configured to reduce leakage from the catheter insertion site when the securement device is secured to the patient's skin; and
   a housing mounted on said base and surrounding said opening, said housing comprising an outer-most annular perimeter wall and an annular top wall extending generally perpendicular from the annular perimeter wall towards the opening to define an annular interior space within the annular perimeter directly below the annular top wall and above the base, the annular interior space configured to receive the catheter therein, wherein said housing is configured such that the catheter coils within said annular interior space, the cover member positioned within the annular perimeter wall of the housing and spaced apart from the annular interior space in a radial direction.

2. The securement device of claim 1, wherein said cover member is hinged to said base at a hinge line.

3. The securement device of claim 2, further comprising a latch device, wherein said cover member latches to said base via said latch device when said cover member is in the closed position.

4. The securement device of claim 1, wherein said cover member further comprises a groove configured to accommodate the catheter, wherein said groove is configured to frictionally engage the catheter without compromising a lumen within the catheter.

5. The securement device of claim 1, wherein said lip surrounds said opening such that when said base is secured to the patient's skin, said lip forces the patient's skin around the catheter to form a seal and reduce leakage from the catheter insertion site.

6. The securement device of claim 5, wherein said lip comprises an arcuate cross-sectional shape.

7. The securement device of claim 1, wherein said housing further comprises one or more slots configured to receive the catheter.

8. The securement device of claim 7, wherein said housing further comprises at least three slots, wherein each of said at least three slots is spaced approximately ninety degrees apart from another one of said at least three slots.

9. The securement device of claim 1, wherein said housing is integral with said base.

10. The securement device of claim 1, further comprising an attachment pad connected to a lower surface of said base, said attachment pad having an adhesive lower surface for attachment to the patient's skin.

11. A securement device assembly, comprising:
    a catheter having a proximal end, a distal end, and walls defining a lumen;
    a securement device, comprising:
      a base configured for attachment to a patient's skin over a catheter insertion site, said base comprising top and bottom surfaces, an opening configured to accommodate the catheter inserted therethrough from the catheter insertion site;
      a cover member configured with said base over said opening, said cover member movable from an open position to a closed position over the catheter insertion site, said cover member configured to secure the catheter;
      a lip configured around at least a portion of said opening on said bottom surface of said base, wherein said lip is configured to reduce leakage from the catheter insertion site when the securement device is secured to the patient's skin; and
      a housing mounted on said base and surrounding said opening, said housing comprising an outer-most annular perimeter wall and an annular top wall extending generally perpendicular from the annular perimeter wall towards the opening to define an annular interior space within the annular perimeter wall directly below the annular top wall and above the base, the annular interior space configured to receive the catheter therein, wherein said housing is configured such that the catheter coils within said annular interior space, the cover member positioned within the annular perimeter wall of the housing and spaced apart from the annular interior space in a radial direction.

12. The securement device assembly of claim 11, wherein said cover member is hinged to said base at a hinge line.

13. The securement device assembly of claim 11, further comprising a latch device, wherein said cover member latches to said base via said latch device when said cover member is in the closed position.

14. The securement device assembly of claim 11, wherein said cover member further comprises a groove configured to accommodate the catheter, wherein said groove is configured to frictionally engage the catheter without compromising a lumen within the catheter.

15. The securement device assembly of claim 11, wherein said lip surrounds said opening such that when said base is secured to the patient's skin, said lip forces the patient's skin around the catheter to form a seal and reduce leakage from the catheter insertion site.

16. The securement device assembly of claim 15, wherein said lip comprises an arcuate cross-sectional shape.

17. The securement device assembly of claim 11, further comprising an attachment pad connected to a lower surface of said base, said attachment pad having an adhesive lower surface for attachment to the patient's skin.

* * * * *